US012788641B2

(12) United States Patent
Green

(10) Patent No.: US 12,788,641 B2
(45) Date of Patent: Nov. 10, 2026

(54) STAY GUARD SURE PAD

(71) Applicant: Christabel Green, Stafford, VA (US)

(72) Inventor: Christabel Green, Stafford, VA (US)

(*) Notice: Subject to any disclaimer, the term of this patent is extended or adjusted under 35 U.S.C. 154(b) by 701 days.

(21) Appl. No.: 18/066,144

(22) Filed: Dec. 14, 2022

(65) Prior Publication Data

US 2024/0197544 A1 Jun. 20, 2024

(51) Int. Cl.
*A61F 13/472* (2006.01)

(52) U.S. Cl.
CPC .. *A61F 13/47227* (2013.01); *A61F 13/47272* (2013.01)

(58) Field of Classification Search
CPC .......... A61F 13/47227; A61F 13/47272; A61F 13/47218
See application file for complete search history.

(56) References Cited

U.S. PATENT DOCUMENTS

2002/0087129 A1* 7/2002 Di Luccio ............... A61L 15/44 604/289
2004/0068244 A1* 4/2004 Salone .................. A61F 13/476 604/385.04
2004/0267220 A1* 12/2004 Hull, Jr. ............ A61F 13/51121 604/380
2006/0025733 A1* 2/2006 Kikuchi .................. A61F 13/42 604/361
2006/0041239 A1* 2/2006 Nagahara .......... A61F 13/15203 604/380
2009/0326502 A1* 12/2009 Konawa .............. A61F 13/4753 604/385.23
2013/0053808 A1* 2/2013 Hill ....................... A61F 13/475 604/377

FOREIGN PATENT DOCUMENTS

JP 2006345909 A * 12/2006 ......... A61F 13/4752
JP 2012157459 A * 8/2012 ......... A61F 13/4704

* cited by examiner

*Primary Examiner* — Susan S Su
(74) *Attorney, Agent, or Firm* — Patent 360; Barry Choobin

(57) ABSTRACT

A sanitary pad for absorbing the human exudate is disclosed. The sanitary pad includes a first surface, a second surface disposed opposite to the first surface, and a raised portion disposed substantially centrally to the sanitary pad and extending outwardly from the first surface. The raised portion is adapted to be inserted, at least partially, within a vestibule of a wearer to facilitate an absorption of mensural fluid of a wearer. Also, the insertion of the raised portion facilitates an alignment and securing of the sanitary pad with the vestibule.

10 Claims, 7 Drawing Sheets

STAY GUARD SURE PAD

TECHNICAL FIELD

The present disclosure relates, generally, to an absorbent article for personal feminine care. The present disclosure more particularly relates to a sanitary pad having a raised portion for positioning, at least partially, within the vestibule of a wearer for absorbing mensural fluid.

BACKGROUND

To provide protection for feminine consumers experiencing conditions leading to the release of the mensural fluid, consumer product manufacturers have developed a wide range of personal care absorbent articles. Sanitary pads are one such absorbent articles having high absorptive capacity. However, the sanitary pads tend to move away from the vaginal orifice due to compressive forces of the wearer's thighs in the pudendal region or during any physical movement, such as walking or any another movement. Such movement of the sanitary pad may lead to leakage of mensural fluid leading to soiling of garments of a wearer which is not desirable.

SUMMARY

According to an aspect of the disclosure, a sanitary pad for absorbing the human exudate is disclosed. The sanitary pad has a first surface and a second surface disposed opposite to the first surface. Further, the sanitary pad includes a raised portion disposed substantially centrally to the sanitary pad and extending outwardly from the first surface. The raised portion is adapted to be inserted, at least partially, within a vestibule of a wearer to facilitate an absorption of mensural fluid of a wearer. Also, the insertion of the raised portion facilitates an alignment and securing of the sanitary pad with the vestibule.

According to another aspect of the disclosure, a sanitary pad for absorbing human exudate is disclosed. The sanitary pad includes a first surface and a second surface disposed opposite to the first surface. Further, the sanitary pad includes a raised portion disposed substantially centrally to the sanitary pad and extending outwardly from the first surface. The raised portion is adapted to be inserted, at least partially, within a vestibule of a wearer for facilitating an absorption of mensural fluid. The insertion of the raised portion facilitates an alignment and securing of the sanitary pad with the vestibule. The sanitary pad further includes a first peripheral portion having a first barrier and a first groove disposed surrounding the raised portion. Furthermore, the sanitary pad includes a second peripheral portion having a second barrier and a second grove disposed spaced apart from the first groove and surrounding the first groove.

According to yet another aspect of the disclosure a sanitary pad for absorbing human exudate is disclosed. The sanitary pad includes a first surface and a second surface disposed opposite to the first surface. The sanitary pad also includes a first raised portion disposed substantially centrally to the sanitary pad and extending outwardly from the first surface. The first raised portion is adapted to be inserted, at least partially, within a vestibule of a wearer for facilitating an absorption of mensural fluid. The insertion of the first raised portion facilitates an alignment and securing of the sanitary pad with the vestibule. Further, the sanitary pad includes a first peripheral portion having a first barrier and a first groove disposed surrounding the first raised portion.

Furthermore, the sanitary pad includes a second peripheral portion having a second barrier and a second groove disposed spaced apart from the first groove and surrounding the first groove. The sanitary pad also includes a second raised portion disposed spaced apart from the first raised portion and extending outwardly from the first surface. The second raised portion is disposed proximate to a second longitudinal end of sanitary pad and is adapted for insertion, at least partially, into an anal region of the wearer.

For a more complete understanding of the present invention, reference is made to the following detailed description and accompanying drawings. In the drawing, like reference characters refer to like parts throughout the views in which:

DETAILED DESCRIPTION

Figure 1:
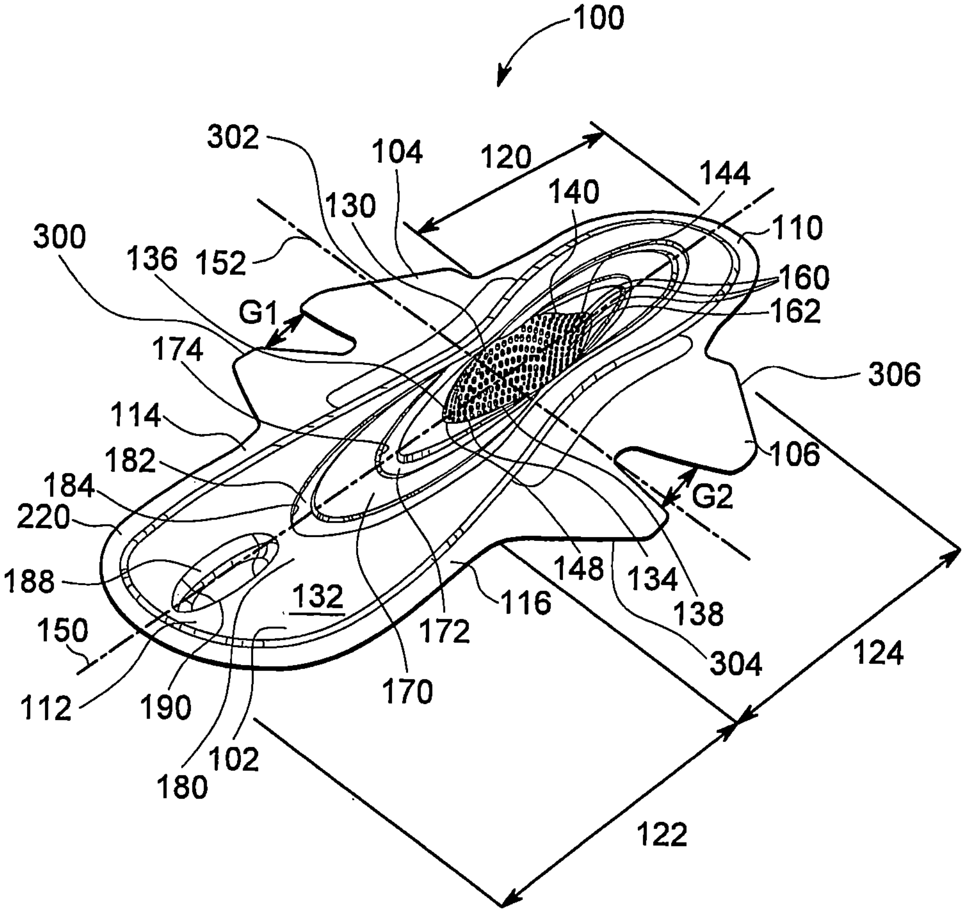
FIG. 1 illustrates to a top perspective view of a sanitary pad, in accordance with an embodiment of the disclosure.
Figure 2:
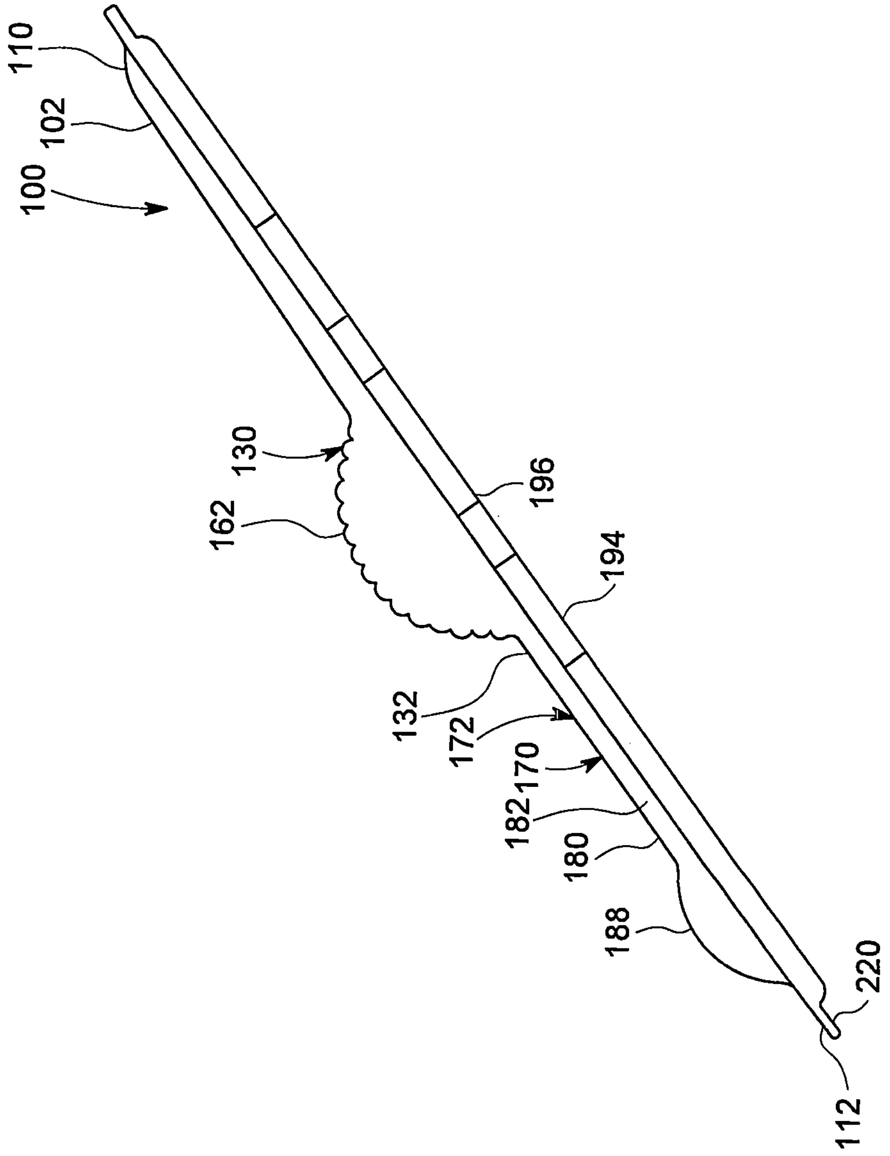
FIG. 2 illustrates to a side view of the sanitary pad of FIG. 1, in accordance with an embodiment of the disclosure.
Figure 4:
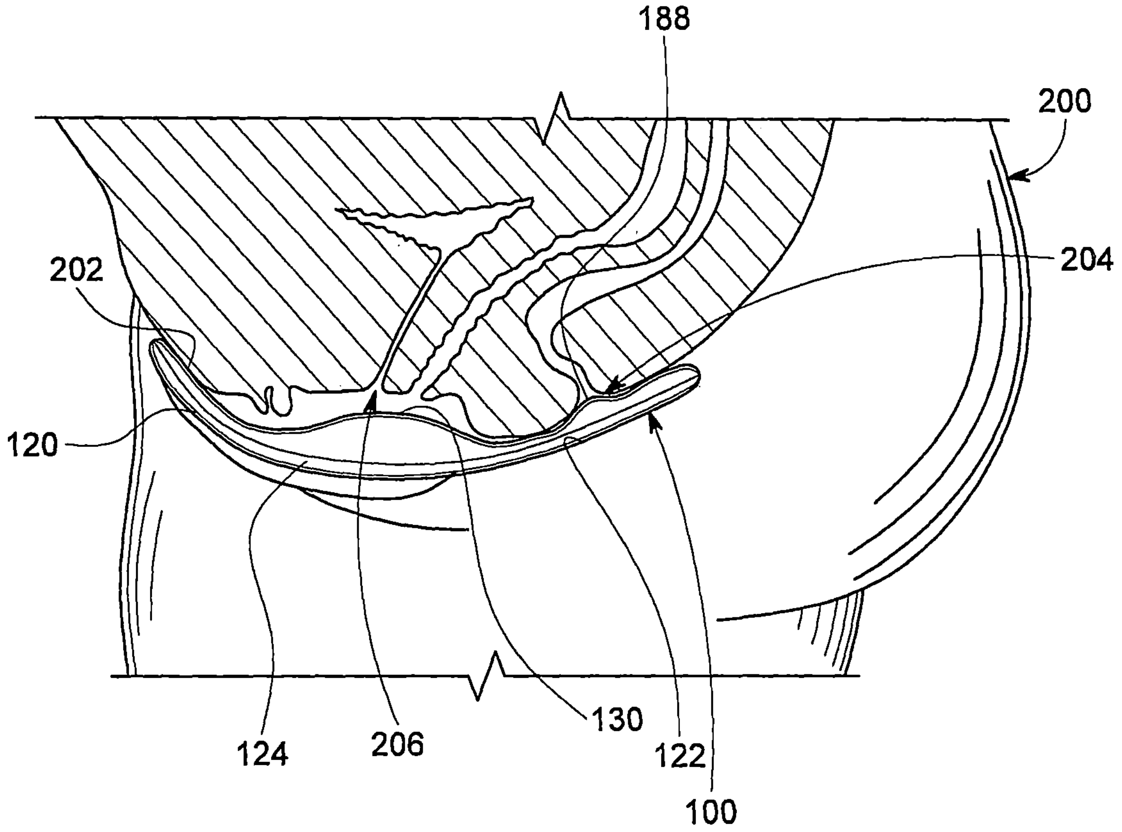
FIG. 4 illustrates a wearer wearing the sanitary pad of FIG. 1, in accordance with an embodiment of the disclosure.

Referring to FIG. 1 and FIG. 2, a sanitary pad 100 (hereinafter referred to as the pad 100) for absorbing a mensural fluid particularly for personal feminine care is shown. As shown, the pad 100 may include an elongated structure 102 and a pair of flaps, for example, a first flap 104 and a second flap 106, disposed substantially centrally to the elongated structure 102 and extending outwardly from the elongated structure 102. The elongated structure 102 includes a first longitudinal end 110, a second longitudinal end 112 disposed spaced apart from the first longitudinal end 110, a first longitudinal side 114 extending between the first longitudinal end 110 and the second longitudinal end 112, and a second longitudinal side 116 disposed opposite to the first longitudinal side 114 extending between the first longitudinal end 110 and the second longitudinal end 112. Further, the elongated structure 102 may include a first portion 120 (hereinafter referred to as a front portion 120), a second portion 122 (hereinafter referred to as a rear portion 122) disposed spaced apart from the front portion 120 and a middle portion 124 disposed between the front portion 120 and the rear portion 122 and extending from the front portion 120 to the rear portion 122. In an embodiment, the front portion 120 extends from the first longitudinal end 110 to the middle portion 124 such that a width of the front portion 120 decreases from the first longitudinal end 110 to the middle portion 124, while the rear portion 122 extends from the second longitudinal end 112 to the middle portion 124 such that a width of the rear portion 122 decreases from the second longitudinal end 112 to the middle portion 124. As shown in FIG. 4, the front portion 120 is adapted to abut/contact at least a portion of pubic mons 202 of a wearer 200, while the rear portion 122 is adapted to abut an anal region 204 of the wearer 200 and may contact, at least partially, buttocks of the wearer 200. Further, the middle portion 124 is adapted to be disposed, at least partly, below a vestibule 206 of the wearer 200 and covering the vestibule 206 of the wearer 200.

Figure 3:
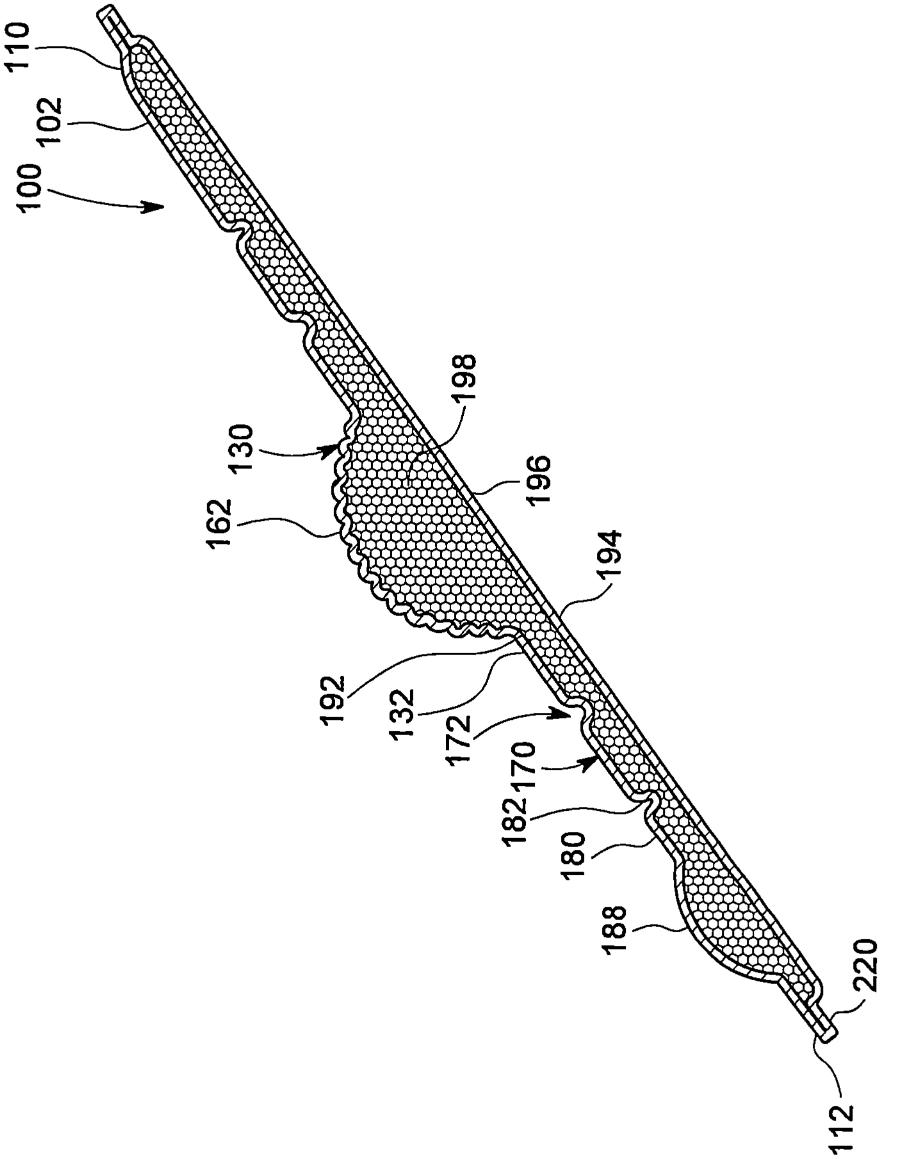
FIG. 3 illustrates a sectional view of the sanitary pad of FIG. 1, in accordance with an embodiment of the disclosure.

As shown in FIGS. 1 to 3, the middle portion 124 includes a raised portion 130 (hereinafter referred to as a first raised portion 130) extending outwardly from a first surface 132 of the pad 100 (i.e. the elongated structure 102) and is adapted to be disposed, at least partially, inside the vestibule 206 when the pad 100 is worn by the wearer 200. In an embodiment, the first raised portion 130 may be disposed centrally to the elongated structure 102, and hence the pad 100, and may include a base 134 connected to the first surface 132, a first side 136 disposed towards the first flap 104 and extending outwardly from the base 134 and the first surface 132, and a second side 138 disposed facing the second flap 106 and extending outwardly from the base 134 and the first surface 132. In an embodiment, the first side 136 includes a substantially convex shape and meets the second side 138 at an edge 140. Similar to the first side 136, the second side 138 may also include a substantially convex shape. As shown, the edge 140 is defined as a line of intersection of the first side 136 and the second side 138, and may extend in a longitudinal direction of the pad 100. Further, as shown, the base 134 includes a first end 144 disposed proximal to the first longitudinal end 110 relative to a second end 148 of the base 134. In an embodiment, the base 134 may include a substantially elliptical shape having a major axis disposed substantially parallel to a longitudinal axis 150 of the pad 100, and a minor axis disposed substantially parallel to a lateral axis 152 of the pad 100. In an embodiment, the minor axis of the base 134 may coincide with the lateral axis 152. Alternatively, the minor axis of the base 134 may be located at an offset from the lateral axis 152. In such a case, a length of the rear portion 122 may be longer than a length of the front portion 120. Further, the first raised portion 130 may include a plurality of microdots 160 extending from an outer surface 162. The plurality of microdots 160 causes in an increase in surface area of the first raised portion 130 and thereby increases a fluid absorption capacity of the first raised portion 130.

Further, the elongated structure 102, and hence the pad 100, includes a first peripheral portion 170 surrounding the first raised portion 130 and may be disposed spaced apart from the first raised portion 130. The first peripheral portion 170 defines a first groove 172 disposed spaced apart from the first raised portion 130 and extending along an entire periphery of the base 134. Therefore, the first groove 172 provides a substantially elliptical channel surrounding the first raised portion 130 for receiving and collecting any fluid flowing from the first raised portion 130. Surrounding the first groove 172 is a first barrier 174 for obstructing the flow of the fluids received inside the first groove 172 to spread across the pad 100. In an embodiment the first barrier 174 may be defined by a raised wall of the first groove 172. Additionally, the elongated structure 102, and hence the pad 100, includes a second peripheral portion 180 disposed surrounding the first peripheral portion 170 and a defining a second groove 182 disposed spaced apart from the first groove 172 and extending along an entire periphery or circumference of the first peripheral portion 170. Therefore, the second groove 182 provides an elliptical channel surrounding the first peripheral portion 170 or the first barrier 174 for receiving and collecting any fluid overflowing from the first groove 172. Surrounding the second groove 182 is a second barrier 184 for obstructing the flow of the fluid received inside the second groove 182 to spread across the pad 100. In an embodiment the second barrier 184 may be defined by a raised wall of the second groove 182.

Additionally, or optionally, the elongated structure 102, and hence the pad 100, includes a second raised portion 188 extending outwardly from the first surface 132, and disposed space apart from the first raised portion 130 and proximate to the second longitudinal end 112. As shown, the second raised portion 188 is disposed along the longitudinal axis 150 and is located between the second groove 182 and the second longitudinal end 11. Further, the second raised portion 188 may include a base 190 that may be substantially elliptical. In such a case, a major axis of the base 190 may be substantially parallel to the longitudinal axis 150, while a minor axis of the base 190 may be substantially parallel to the lateral axis 152. In an embodiment, the major axis of the base 134 of the first raised portion 130 and the major axis of the base 190 of the second raised portion 188 coincide with the longitudinal axis 150. In an embodiment, the second raised portion 188 may include a height smaller than a height of the first raised portion 130, and a length smaller than a length of the first raised portion 130. The second raised portion 188 is adapted for insertion into the anal region 204 between the buttocks of the wearer 200 for providing a leak proof packaging of the pad 100 between the vestibule 206 and the buttocks of the wearer 200. In this manner, the second raised portion 188 facilitates for the proper alignment of the pad 100 when the wearer 200 is lying on the side or during sleeping positions. Further, the first flap 104 includes two portions 300,302 separated by a first gap 'G1'. Similarly, the second flap 106 also includes two portions 304, 306 separated by a second gap 'G2'.

Further, as shown in FIG. 3, the elongated structure 102, and hence the pad 100, may include a first layer 192 defining the first surface 132 and adapted to abut a body of the wearer 200, a second layer 194 disposed opposite to the first layer 192 and defining a second surface 196 of the pad 100. Further, the elongated structure 102 includes a third layer 198 sandwiched between the first layer 192 and the second layer 194. In an embodiment, the third layer 198 is formed of an absorbent material to absorb any fluid flowing from the body of the wearer 200. The absorbent material may include a wide variety of liquid-absorbing material used for absorbing the mensural fluids. For example, the absorbent material may include cotton fibers or cotton lintels, creped cellulose wadding, meltblown polymers including coform, chemically stiffened, modified or cross-linked cellulosic fibers, synthetic fibers such as crimped polyester fibers, peat moss, tissue including tissue wraps and tissue laminates, absorbing foams, absorbing sponges, superabsorbent polymers (in fibrous and particulate form); absorbing gelling materials, or any equivalent material or combinations of materials, or mixtures known in the art.

To facilitate absorption of the fluid by the third layer 198, the first layer 192 is a liquid permeable layer, while the second layer 194 is a liquid impermeable layer to prevent a leakage of the fluid through the pad 100. In certain implementations, the first layer 192 may suitably be made from a soft, textile like material or non-woven-fabric. Other example of the suitable material is perforated plastic film, knitted or woven textiles as well as combination and laminates of multiple materials. Also, the second layer 194 may include polymer films of polyethylene and polypropylene. As shown in FIG. 1, the first layer 192 and the second layer 194 attached together along the periphery to retain the absorbent, and hence the third layer 198, between the first layer 192 and the second layer 194. The attached portion defines a bonier 220 of the pad 100.

Figure 5:
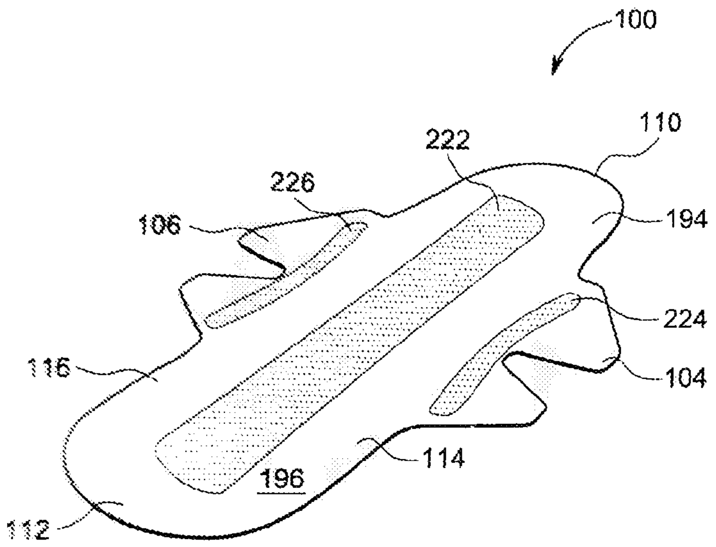
FIG. 5 illustrates to a bottom perspective view of the sanitary pad of FIG. 1, in accordance with an embodiment of the disclosure.

Referring to FIG. 5, a bottom view of the pad 100 is shown. As shown, the pad 100 may include a plurality of adhesive strip for example a first adhesive strip 222, a second adhesive strip 224, and a third adhesive strip 226 positioned on the second surface 196. The first adhesive strip 222 may extend in a longitudinal direction between the first longitudinal end 110 and the second longitudinal end 112, and may be disposed centrally to the pad 100. The first adhesive strip 222 facilitates a sticking of the pad 100 with an undergarment of the wearer 200. Further, the second adhesive strip 224 may be disposed on the first flap 104, while the third adhesive strip 226 may be disposed on the second flap 106. The second adhesive strip 224 and the third adhesive strip 226 may facilitate the sticking of the pair of flaps 104, 106 to the undergarment of the wearer 200 providing a secure attachment of the pad 100. Also, the plurality of adhesive strips 222, 224 and 226 may be covered with paper strips (not shown) to be released/removed when the pad 100 is to be used by the wearer 200.

Figure 6:
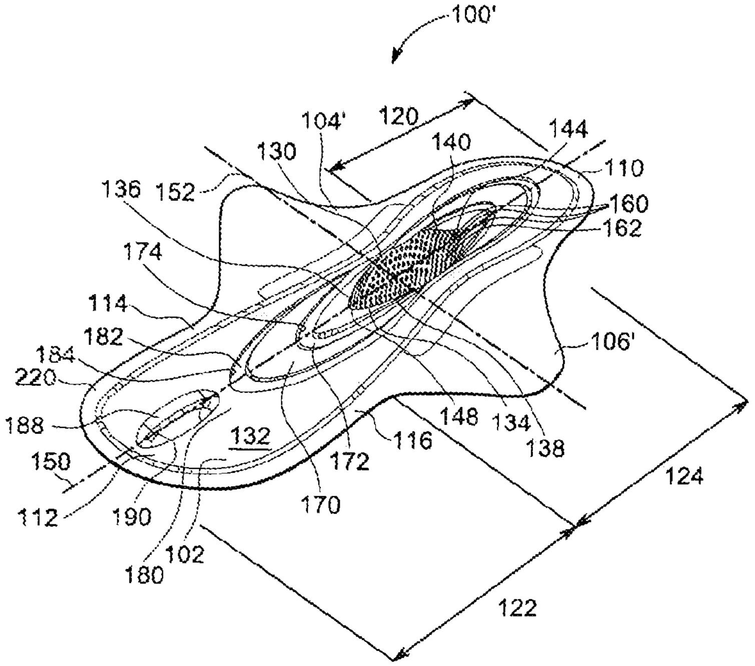
FIG. 6 illustrates to a top perspective view of a sanitary pad, in accordance with an alternative embodiment of the disclosure.

Referring to FIG. 6, a sanitary pad 100' (hereinafter referred to as the pad 100') is shown. The pad 100' is similar in structure, construction, and function to that of pad 100 except the pad 100' includes a pair of flaps 104', 106' that are different from the pair of flaps 104, 106. Further, the elements of the pad 100 have similar construction and structural aspects as that of the elements of the pad 100 and will have same reference numerals. As shown, the flaps 104', 106', each include a single portion as compared to the flaps 104, 106, each having two portions.

Figure 7:
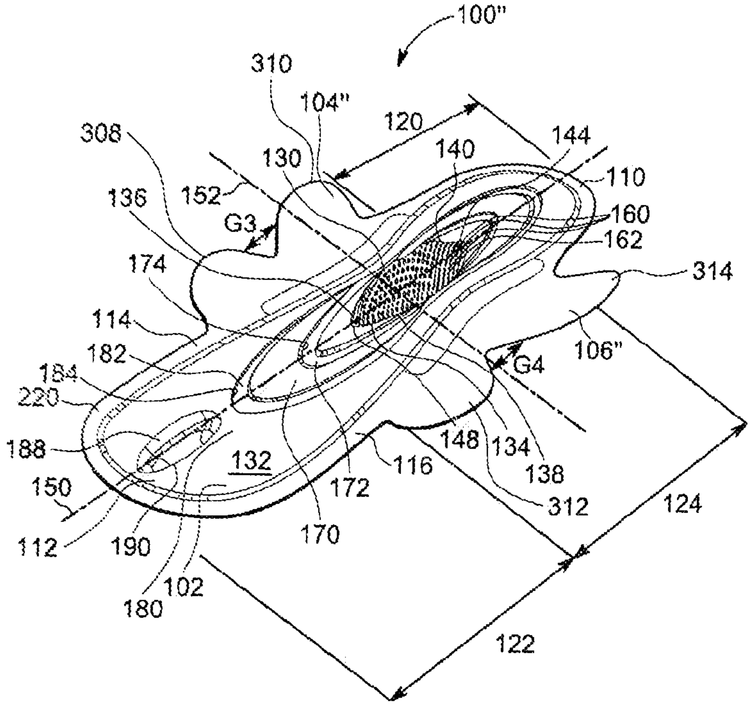
FIG. 7 illustrates to a top perspective view of a sanitary pad, in accordance with yet another embodiment of the disclosure.

Referring to FIG. 7, a sanitary pad 100" (hereinafter referred to as the pad 100") is shown. The pad 100" is similar in structure, construction, and function to that of pad 100 except the pad 100" includes a pair of flaps 104", 106" that are different from the pair of flaps 104, 106. Further, the elements of the pad 100' have similar construction and structural aspects as that of the elements of the pad 100 and will have same reference numerals. As shown, the flap 104" includes two portions 308, 310 separated by a gap G3. The gap G3 is larger than the gap 'G1' such the two portions resemble wings of a butterfly. Similarly, the flap 106" includes two portions 312, 314 separated by a gap 'G4'. The gap 'G4' is larger than the gap 'G2' such the two portions 312, 314 resemble wings of a butterfly.

An application of the pad 100, 100' and 100" is now disclosed. When the pad 100, 100' and 100" is worn by the wearer 200, a portion of the first raised portion 130 is disposed/inserted inside the vestibule 206 of the wearer 200. The partial insertion of the first raised portion 130 in the vestibule 206 of the wearer 200 facilitates a rapid absorption of the mensural fluid. Also, the partially inserted first raised portion 130 ensures a higher absorption of the mensural fluid by residing inside the vaginal cavity and occluding the flow of mensural fluid. Further, the insertion of the first raised portion 130 inside the vestibule 206 and an insertion of the second raised portion 188 inside the anal region 204 ensure a proper alignment of the pad 100, 100', and 100" and prevent any movement of the pad 100, 100' and 100" relative to the body of the wearer 200.

It should be understood that the foregoing description is only illustrative of the aspects of the disclosed embodiments. Various alternatives and modifications can be devised by those skilled in the art without departing from the aspects of the disclosed embodiments. Accordingly, the aspects of the disclosed embodiments are intended to embrace all such alternatives, modifications, and variances that fall within the scope of the appended claims. Further, the mere fact that different features are recited in mutually different dependent or independent claims does not indicate that a combination of these features cannot be advantageously used, such as a combination remaining within the scope of the aspects of the disclosed embodiments.

LIST OF ELEMENTS

100 sanitary pad
100' sanitary pad
100" sanitary pad
102 elongated structure
104 first flap
104' first flap
104" first flap
second flap
106' second flap
106" second flap
110 first longitudinal end
112 second longitudinal end
114 first longitudinal side
116 second longitudinal side
120 first portion
122 second portion
124 middle portion
130 raised portion
132 first surface
134 base
136 first side
138 second side
144 first end
148 second end
150 longitudinal axis
152 lateral axis
160 dots
162 outer surface
170 first peripheral portion
172 first groove
174 first barrier
182 second groove
184 second barrier
188 second raised portion
190 base
192 first layer
194 second layer
196 second surface
198 third layer
200 wearer
202 pubic mons
204 anal region
206 vestibule
220 border
222 first adhesive strip
224 second adhesive strip
226 third adhesive strip
300 portion
302 portion
304 portion
306 portion
308 portion
310 portion
312 portion
314 portion
G1 gap
G2 gap
G3 gap G4 gap

What is claimed is:

1. A sanitary pad for absorbing human exudate, the sanitary pad having an elongated structure, the elongated structure having a first surface and a second surface disposed opposite to the first surface, a first longitudinal end, and a second longitudinal end, the sanitary pad comprising:

a first raised portion disposed substantially centrally to the elongated structure and extending outwardly from the first surface, the first raised portion is adapted to be inserted, at least partially, within a vestibule of a wearer for facilitating an absorption of menstrual fluid, wherein the insertion of the first raised portion facilitates an alignment and securing of the sanitary pad with the vestibule;

a left flap and a right flap extending from left and right sides of the elongated structure respectively;

a first peripheral portion defining a first groove disposed spaced apart from the first raised portion and extending along an entire periphery of the first raised portion such that the first groove completely surrounds the first raised portion, and surrounding the first groove is a raised first barrier;

a second peripheral portion disposed surrounding the first peripheral portion, the second peripheral portion defining a second groove completely surrounding the first peripheral portion, and surrounding the second groove is a raised second barrier;

a second raised portion disposed spaced apart from the first raised portion and extending outwardly from the first surface, wherein the second raised portion is disposed proximate to the second longitudinal end of the sanitary pad and is adapted for insertion, at least partially, into an anal region of the wearer, wherein the second raised portion is located more rearward on the sanitary pad than the first groove and the second groove such that the second raised portion remains entirely outside of the first groove and the second groove, and wherein the first raised portion and the second raised portion are separated by the first groove and the second groove;

a top layer defining the first surface;

a second layer defining the second surface;

a third layer made of absorbent material sandwiched between the first layer and the second layer; and a plurality of adhesive strips coupled to the second surface.

2. The sanitary pad of claim 1, wherein the first raised portion includes a plurality of microdots extending outwardly from an outer surface of the first raised portion.

3. The sanitary pad of claim 1, wherein the first raised portion is of a substantially elliptical shape including a major axis aligned with a longitudinal axis of the sanitary pad.

4. The sanitary pad of claim 1, wherein the second raised portion is elliptical and protruding in shape, and aligns with the first raised portion in a longitudinal direction.

5. The sanitary pad of claim 1, wherein each of the left flap and the right flap comprises two wing shape flaps separated by a predefined gap.

6. The sanitary pad of claim 1, wherein the top layer is liquid permeable and the second layer is liquid impermeable.

7. A sanitary pad for absorbing human exudate, the sanitary pad having a first surface and a second surface disposed opposite to the first surface, a first longitudinal end, and a second longitudinal end, the sanitary pad comprising:

a first raised portion disposed substantially centrally to the sanitary pad and extending outwardly from the first surface, the first raised portion is adapted to be inserted, at least partially, within a vestibule of a wearer for facilitating an absorption of menstrual fluid, wherein an insertion of the first raised portion facilitates an alignment and securing of the sanitary pad with the vestibule;

a first peripheral portion having a first barrier and a first groove disposed spaced apart from the first raised portion and extending along an entire periphery of the first raised portion such that the first groove completely surrounds the first raised portion;

a second peripheral portion having a second barrier and a second groove disposed spaced apart from the first groove and completely surrounding the first groove; and a second raised portion disposed spaced apart from the first raised portion and extending outwardly from the first surface, wherein the second raised portion is disposed proximate to the second longitudinal end of the sanitary pad and is adapted for insertion, at least partially, into an anal region of the wearer, wherein the second raised portion is located more rearward on the sanitary pad than the first groove and the second groove such that the second raised portion remains entirely outside of the first groove and the second groove, and wherein the first raised portion and the second raised portion are separated by the first groove and the second groove.

8. The sanitary pad of claim 7, wherein the first raised portion includes a plurality of microdots extending outwardly from an outer surface of the first raised portion.

9. The sanitary pad of claim 7, wherein the first raised portion includes a base having a substantially elliptical shape including a major axis aligned with a longitudinal axis of the sanitary pad.

10. The sanitary pad of claim 7, wherein the second raised portion is elliptical and protruding in shape, and aligns with the first raised portion in a longitudinal direction.

* * * * *